United States Patent
Mazzillo et al.

(10) Patent No.: US 9,671,351 B2
(45) Date of Patent: Jun. 6, 2017

(54) MULTI-SENSOR OPTICAL DEVICE FOR DETECTING CHEMICAL SPECIES AND MANUFACTURING METHOD THEREOF

(71) Applicant: STMICROELECTRONICS S.R.L., Agrate Brianza (IT)

(72) Inventors: Massimo Cataldo Mazzillo, Corato (IT); Alfio Russo, Biancavilla (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 256 days.

(21) Appl. No.: 14/659,038

(22) Filed: Mar. 16, 2015

(65) Prior Publication Data
US 2015/0308962 A1 Oct. 29, 2015

(30) Foreign Application Priority Data
Apr. 24, 2014 (IT) .............................. TO2014A0342

(51) Int. Cl.
| | | |
|---|---|---|
| *G01N 21/85* | (2006.01) | |
| *G01N 21/31* | (2006.01) | |
| *G01N 21/05* | (2006.01) | |
| *H01L 31/18* | (2006.01) | |
| *H01L 31/0216* | (2014.01) | |
| *G01N 21/61* | (2006.01) | |
| *H01L 31/00* | (2006.01) | |
| *G01N 21/33* | (2006.01) | |

(52) U.S. Cl.
CPC ............. *G01N 21/85* (2013.01); *G01N 21/05* (2013.01); *G01N 21/31* (2013.01); *G01N 21/314* (2013.01);
(Continued)

(58) Field of Classification Search
CPC ...... G01N 21/85; G01N 21/314; G01N 21/05; H01L 31/18; H01L 31/00
(Continued)

(56) References Cited

U.S. PATENT DOCUMENTS

| 5,041,723 A | 8/1991 | Ishida et al. |
| 5,241,367 A * | 8/1993 | Grob .................... G01N 21/534 |
| | | 250/575 |

(Continued)

FOREIGN PATENT DOCUMENTS

| CN | 102608183 A | 7/2012 |
| DE | 10 2005 033 639 A1 | 1/2007 |

(Continued)

OTHER PUBLICATIONS

SICK Sensor Intelligence, "DEFOR: Extractive UV Gas Analyzer," SICK MAIHAK GmbH, Apr. 2009, obtained from http://www.baytec-inc.com/pdf/defor-extractive-analyzer.pdf on Mar. 16, 2015, 4 pages.

(Continued)

*Primary Examiner* — Seung C Sohn
(74) *Attorney, Agent, or Firm* — Seed IP Law Group LLP

(57) ABSTRACT

An optical device for detecting a first chemical species and a second chemical species contained in a specimen, which includes: a first optical sensor, which may be optically coupled to an optical source through the specimen and is sensitive to radiation having a wavelength comprised in a first range of wavelengths; and a second optical sensor, which may be optically coupled to the optical source through the specimen and is sensitive to radiation having a wavelength comprised in a second range of wavelengths, different from the first range of wavelengths.

22 Claims, 10 Drawing Sheets

(52) U.S. Cl.
CPC .............. *G01N 21/61* (2013.01); *H01L 31/00* (2013.01); *H01L 31/02162* (2013.01); *H01L 31/18* (2013.01); *G01N 21/33* (2013.01); *G01N 2021/3137* (2013.01); *G01N 2021/8578* (2013.01); *G01N 2201/0612* (2013.01)

(58) Field of Classification Search
USPC .............................................. 250/573, 222.1
See application file for complete search history.

(56) References Cited

U.S. PATENT DOCUMENTS

| | | | | |
|---|---|---|---|---|
| 5,777,748 | A | * | 7/1998 | Stengel ................. G01N 21/532 |
| | | | | 250/574 |
| 8,648,322 | B2 | * | 2/2014 | Lindner ................. G01N 15/10 |
| | | | | 250/573 |
| 2011/0168557 | A1 | | 7/2011 | Park et al. |

FOREIGN PATENT DOCUMENTS

| | | |
|---|---|---|
| JP | 2008-241581 A | 10/2008 |
| WO | 2005/064315 A1 | 7/2005 |

OTHER PUBLICATIONS

Monroy et al., "AlGaN-based UV photodetectors," *Journal of Crystal Growth* 230:537-543, 2001.
Morkoç et al., "GaN-based modulation doped FETs and UV detectors," *Solid-State Electronics* 46:157-202, 2002.

* cited by examiner

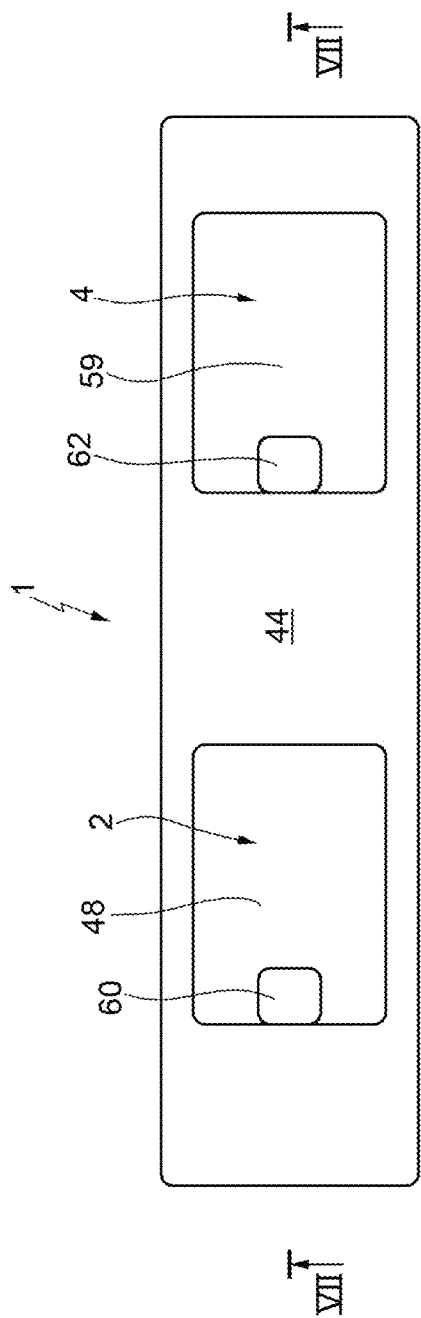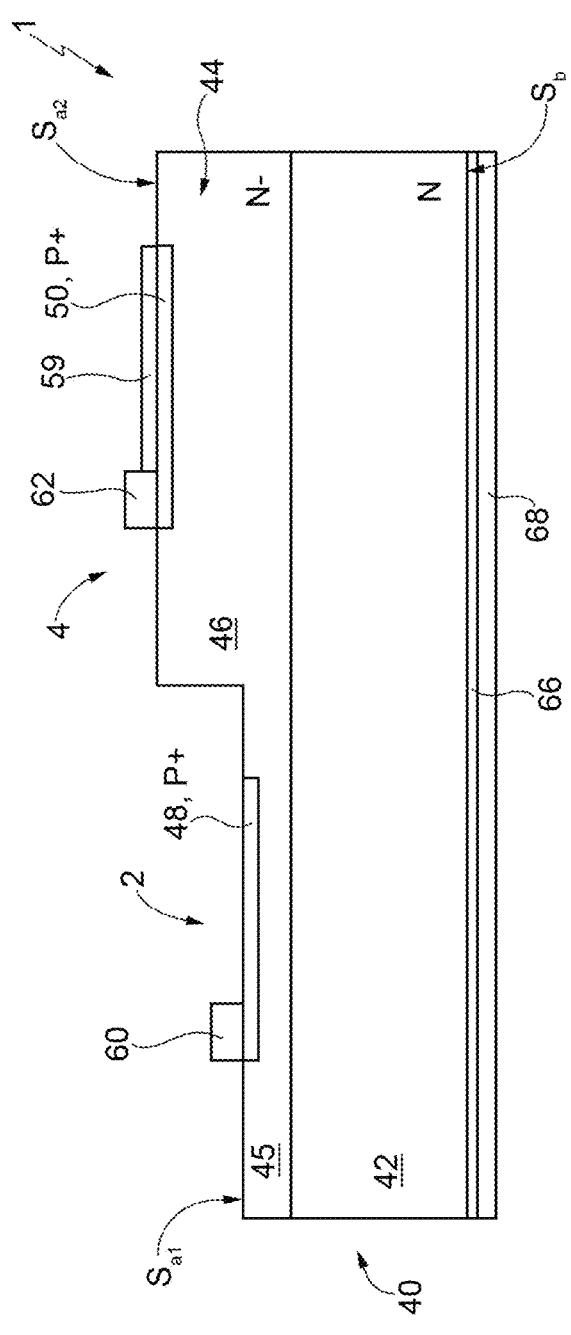

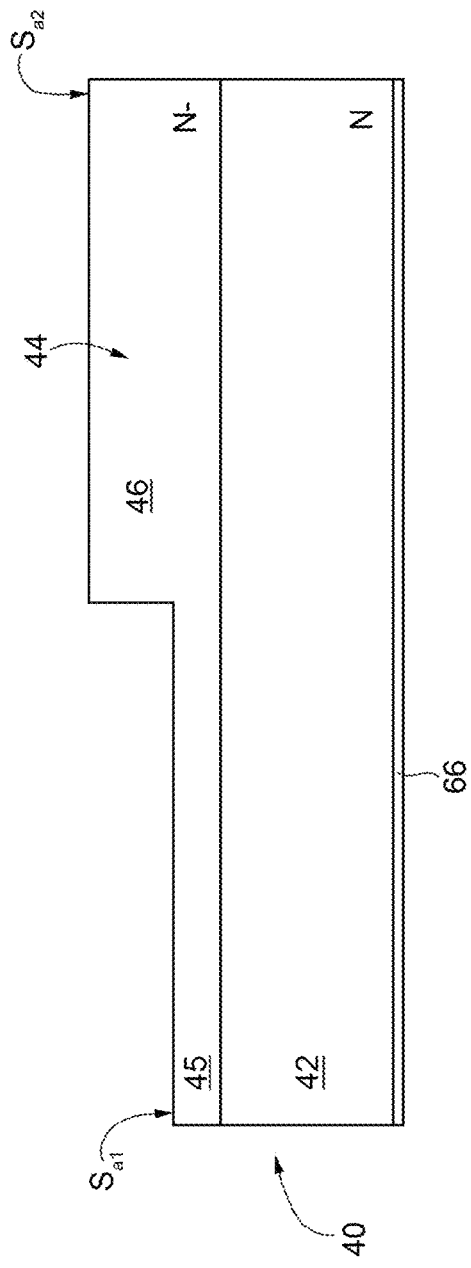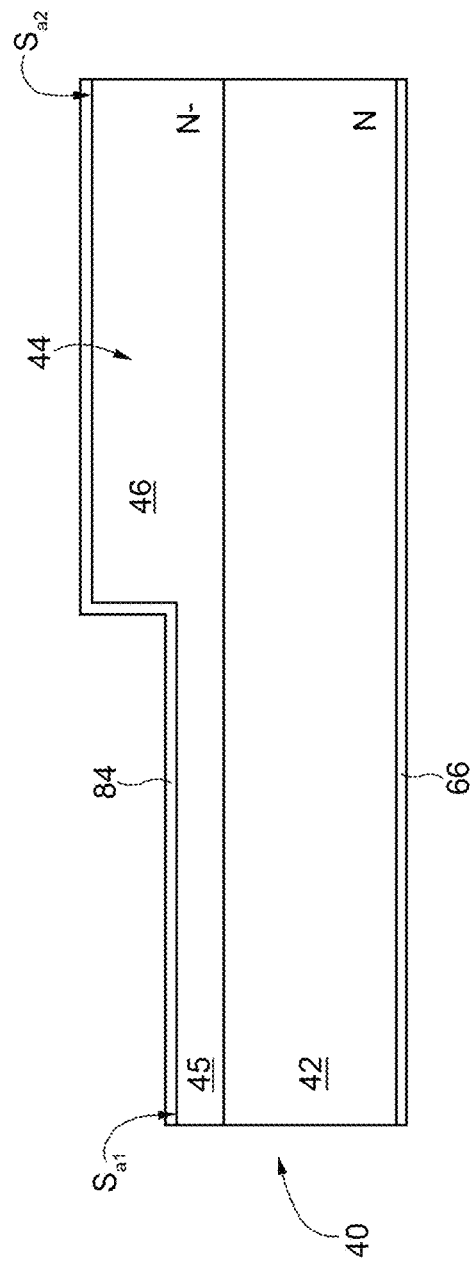

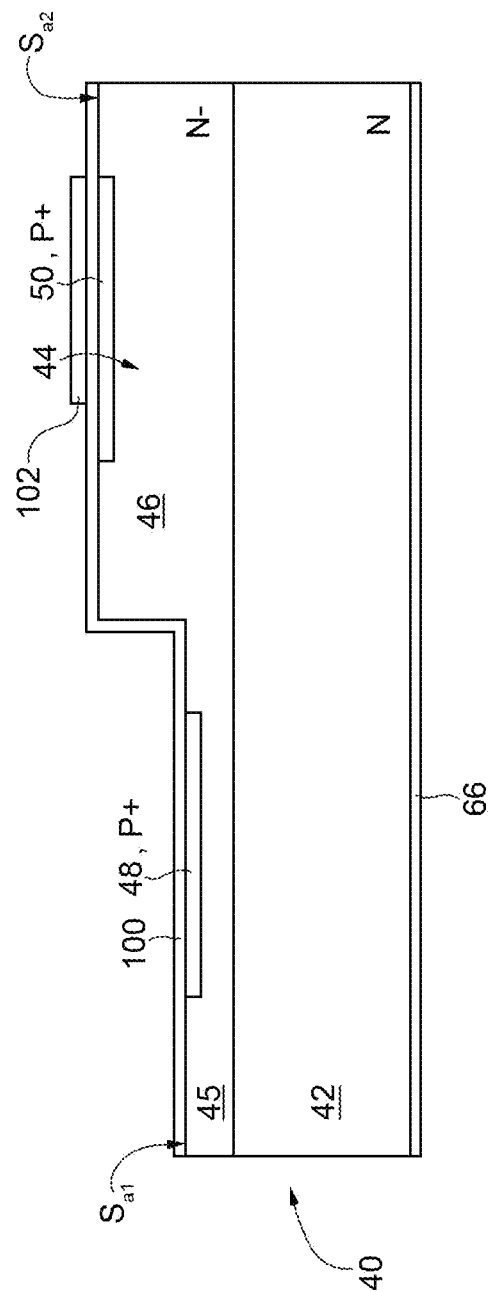

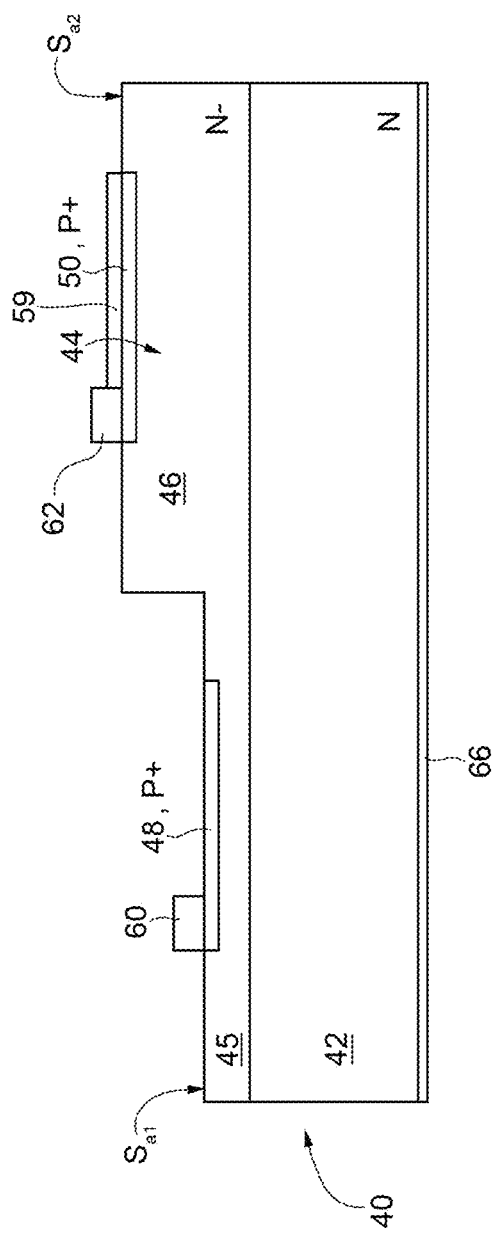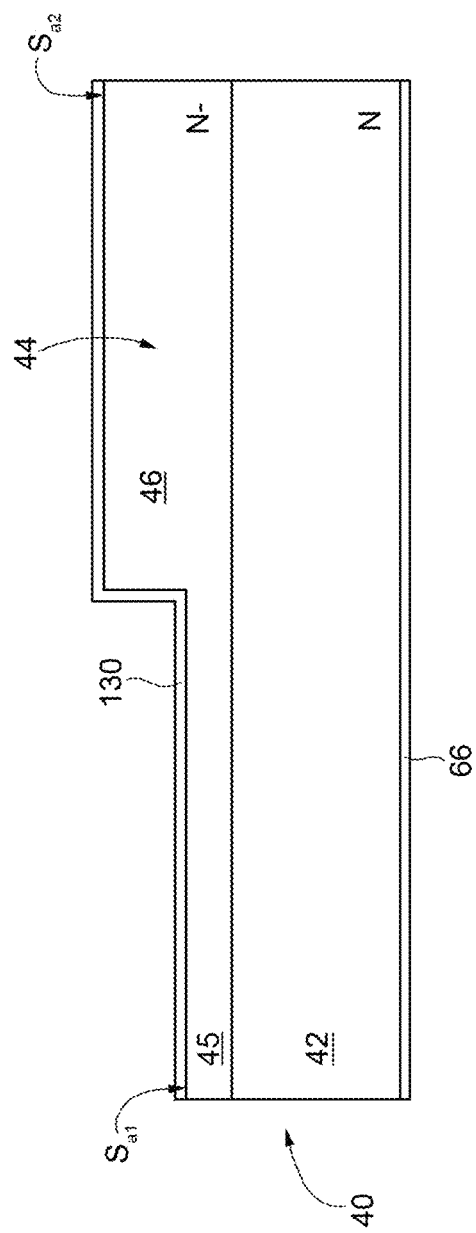

MULTI-SENSOR OPTICAL DEVICE FOR DETECTING CHEMICAL SPECIES AND MANUFACTURING METHOD THEREOF

BACKGROUND

Technical Field

The present disclosure relates to a multi-sensor optical device for detecting chemical species, as well as to the manufacturing method thereof.

Description of the Related Art

As is known, in different fields of application one can detect one or more chemical species and then determine the corresponding concentrations of these chemical species. For instance, in the motor-industry sector, one can determine the concentrations, in an exhaust gas, of chemical species that are generated in the course of the thermal reactions that take place within an engine.

Once again with reference to the motor-industry sector, it is known that, following upon a combustion reaction that occurs between the fuel and the air, water ($H_2O$), carbon dioxide ($CO_2$), carbon monoxide (CO), sulphur oxides ($SO_x$), nitrogen oxides ($NO_x$), hydrocarbons (HC) and particulate matter (PM) are generated. In addition, nitrogen oxides include nitrogen monoxide (NO), nitrogen dioxide ($NO_2$), and dinitrogen oxide ($N_2O$).

Since the chemical species resulting from a combustion reaction concur significantly in pollution, the control of the levels of emission of these chemical species proves to be of particular importance. Consequently, various types of sensors have been developed over time, referred to in general as burnt-gas sensors. For instance, different types of nitrogen-oxide sensors are known, which are commonly employed within closed control loops that are designed to control the combustion process.

Since the aforementioned burnt-gas sensors usually operate in extreme environmental conditions, they are characterized not only by high sensitivity and speeds of response, but also by a considerable resistance to high temperatures, as well as to corrosive chemical agents. For this reason, known sensors are of silicon carbide (SiC), as described, for example, in the patent application no. DE20051033639. In this patent application a sensor is described including a sensing region of porous material, coated with a functional layer, capable of reacting with the chemical species to be analyzed; the reaction involves a detectable variation of the concentration of the carriers within the functional layer.

In general, burnt-gas sensors based upon the variation, following upon absorption of a chemical species by a constitutive element thereof, of an electrical characteristic of this element are characterized by low costs and by a certain simplicity of construction; however, they are likewise characterized by a not particularly high sensitivity, as well as, at times, by a low selectivity in regard to the chemical species absorbed. In addition, these sensors are far from suited to operating in the presence of corrosive chemical agents.

Commercial products are likewise known of the type described in the document available at http://www.baytec-inc.com/pdf/defor-extractive-analyzer.pdf. Illustrated in this document is a gas analyzer including a source of UV radiation and two optical detectors. Further, the analyzer enables detection of more than one chemical species, thanks to the use of a motor-driven mobile element, constrained to which is an optical filter so that the optical filter may be coupled to one of the optical detectors in a controlled way. Even though this system is characterized by a high accuracy, it may not be integrated; thus, it presents large overall dimensions and a high complexity. Consequently, this system is mainly suited for laboratory tests.

BRIEF SUMMARY

According to the present disclosure, a device for detecting chemical species and a manufacturing method thereof are consequently provided. One embodiment of the present disclosure is directed to an optical device that includes an optical source, a first optical sensor configured to be optically coupled to the optical source through a specimen, the specimen having a first chemical species and a second chemical species, the first optical sensor being sensitive to radiation having a wavelength in a first range of wavelengths, and a second optical sensor configured to be optically coupled to the optical source through the specimen, the second optical sensor being sensitive to radiation having a wavelength in a second range of wavelengths, different from the first range of wavelengths.

BRIEF DESCRIPTION OF THE SEVERAL VIEWS OF THE DRAWINGS

For a better understanding of the present disclosure, preferred embodiments thereof are now described, purely by way of non-limiting example and with reference to the attached drawings, wherein:

FIG. 6 is a schematic top plan view of an embodiment of the present detection device;

FIG. 7 is a schematic cross-sectional view of the embodiment represented in FIG. 6, taken along a line of section VII-VII shown in FIG. 6;

FIGS. 10-20 are schematic cross-sectional views of embodiments of the present detection device, during successive steps of a manufacturing method.

DETAILED DESCRIPTION

Figure 1:
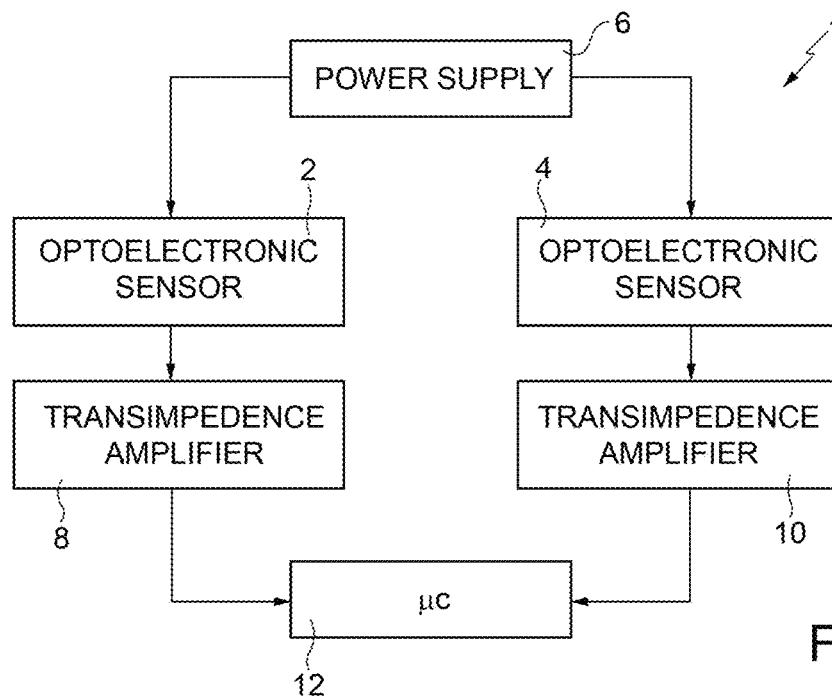
FIG. 1 shows a block diagram of the present device for detecting chemical species.

FIG. 1 shows a device for detecting chemical species 1, which will be referred to hereinafter, for brevity, as "detection device 1".

The detection device 1 comprises a first optoelectronic sensor 2 and a second optoelectronic sensor 4, and a power supply 6, which is designed to bias the first and second optoelectronic sensors 2, 4, to which it is electrically connected. Furthermore, the detection device 1 comprises a first amplifier 8 and a second amplifier 10, for example of the transimpedence type, and a processing unit 12.

Figure 2:
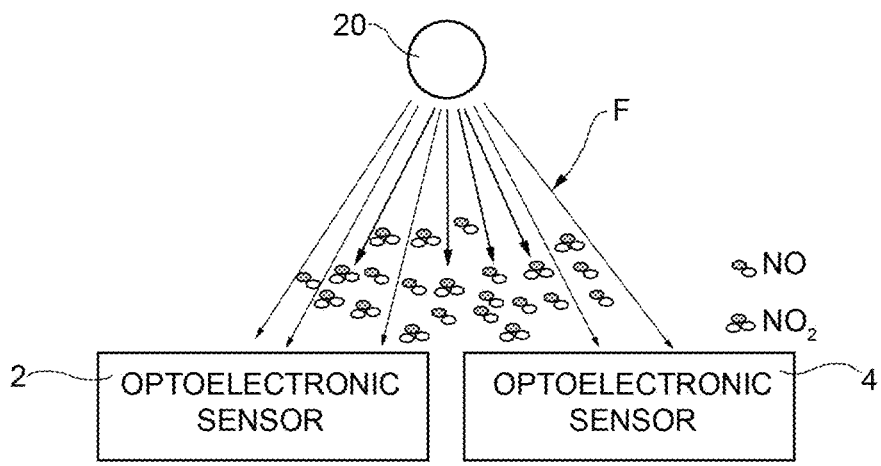
FIG. 2 shows qualitatively a principle diagram of operation of the present detection device.

The detection device 1 likewise comprises, as illustrated in FIG. 2 and described in greater detail hereinafter, an optical source 20 designed to generate radiation that impinges, in use, upon the first and second optoelectronic sensors 2, 4. Furthermore, in use, a fluid F is arranged between the optical source 20 and the first and second optoelectronic sensors 2, 4, so that the radiation generated by the optical source 20 traverses the fluid F before impinging upon the first and second optoelectronic sensors 2, 4. In turn, the first and second optoelectronic sensors 2, 4 generate a first electrical signal and a second electrical signal, which will be referred to as "first and second detection signals". The first and second detection signals are supplied, respectively, to the first and second amplifiers 8, 10 and indicate the intensity of the radiation that impinges, respectively, upon the first and second optoelectronic sensors 2, 4. In turn, the first and second amplifiers 8, 10 generate, on the basis of the first and second detection signals, a first further signal and a second further signal, which will be referred to hereinafter as "first and second processable signals". These first and second processable signals are supplied to the processing unit 12, which executes the processing operations described in what follows.

Figure 3A:
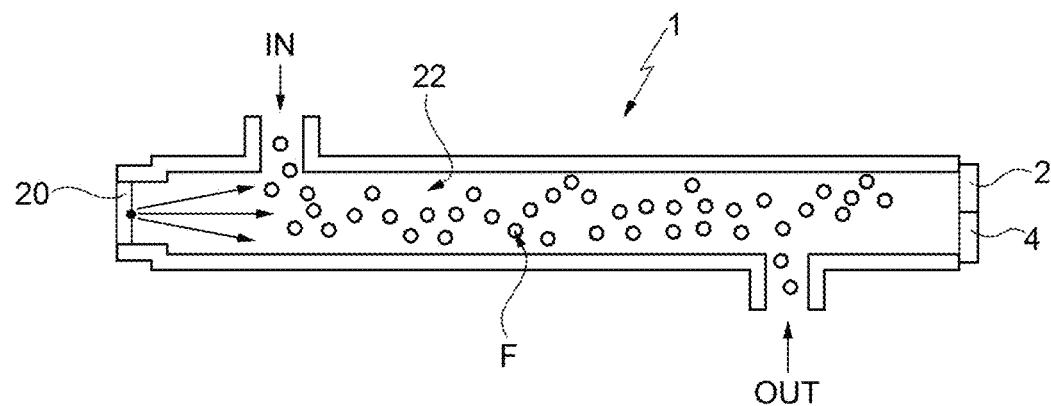
FIGS. 3A and 3B are schematic cross-sectional views of embodiments of the present detection device.

As illustrated in greater detail in FIG. 3A, the detection device 1 comprises a chamber 22, which enables functional coupling of the optical source 20, the first and second optoelectronic sensors 2, 4, and the fluid F. In particular, the chamber 22 has a fluid inlet IN and a fluid outlet OUT, by which the fluid F can, respectively, enter and exit from the chamber 22. Furthermore, the optical source 20 is arranged at a first end of the chamber 22, whereas the first and second optoelectronic sensors 2, 4 are arranged at a second end of the chamber 22. In this way, the radiation generated by the optical source 20 traverses a portion of the chamber 22, and thus passes through the fluid F, before impinging upon the first and second optoelectronic sensors 2, 4.

Figure 3B:
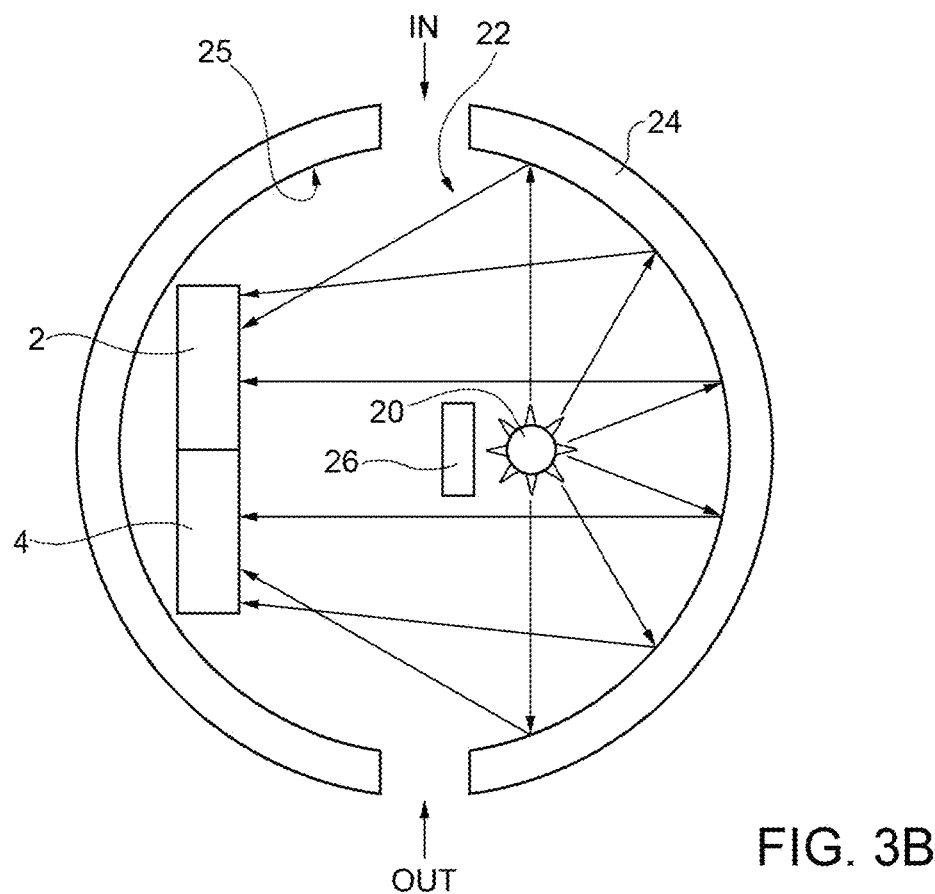

However possible are variants in which the optical coupling between the optical source 20 and the first and second optoelectronic sensors 2, 4 is obtained in a different way and/or the chamber 22 has a different shape. Purely by way of example, it is for instance possible that, as illustrated in FIG. 3B, the chamber 22 is formed by a spherical container 24, which, in addition to forming the fluid inlet IN and the fluid outlet OUT, has an inner wall 25 having a substantially spherical shape (but for the fluid inlet and outlet) and is designed to reflect the radiation generated by the optical source 20. More in particular, the first and second optoelectronic sensors 2, 4 and the optical source 20 are arranged within the chamber 22, together with a screen 26 of a reflecting type. In addition, the screen 26 is arranged between the optical source 20 and the first and second optoelectronic sensors 2, 4 so that the radiation generated by the optical source 26 may not impinge upon the first and second optoelectronic sensors 2, 4, other than after being reflected at least once by the inner wall 25. In this way, the length of the optical paths that connect the optical source 20 to the first and second optoelectronic sensors 2, 4 is increased, given the same overall dimensions of the chamber 22.

Figure 4:
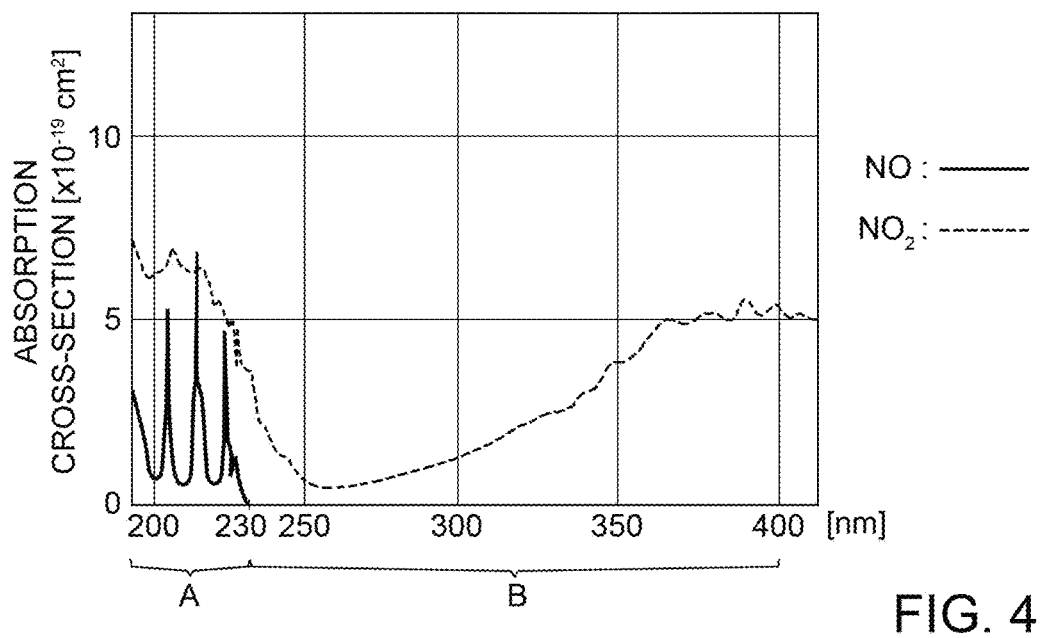
FIG. 4 shows qualitatively the plots of the absorption cross-sections for nitrogen monoxide NO and nitrogen dioxide $NO_2$, expressed in $\times 10^{-19}$ $cm^2$ and as a function of the wavelength ($\lambda$)

This being said, in what follows reference will be made, without this implying any loss of generality, to the case where the detection device 1 is designed to detect individually nitrogen monoxide NO and nitrogen dioxide $NO_2$, i.e., to determine the individual concentrations of nitrogen monoxide NO and nitrogen dioxide $NO_2$ present in the fluid F. In this connection, FIG. 4 shows the plots of the absorption cross-sections for nitrogen monoxide NO and nitrogen dioxide $NO_2$, expressed in $x10^{-19}$ $cm^2$ and as a function of the wavelength ($\lambda$). In this case, without this implying any loss of generality, the optical source 20 emits UV radiation. For instance, without this implying any loss of generality, it is assumed that this radiation has a constant spectrum in the range 200-400 nm. For practical purposes, the optical source 20 may be formed by a voltaic-arc lamp, or else by a LED or laser diode.

It is likewise assumed, without this implying any loss of generality, that the first and second optoelectronic sensors 2, 4 are semiconductor sensors at least in part of silicon carbide, as described hereinafter. Furthermore, it is assumed that the first optoelectronic sensor 2 is sensitive to radiation having a wavelength comprised in a first range of 200-230 nm, designated by A in FIG. 4; it is further assumed that the second optoelectronic sensor 4 is sensitive to radiation having a wavelength comprised in a second range of 230-400 nm. In practice, it is known that nitrogen monoxide NO absorbs below 230 nm, and thus in the range 200-230 nm, as it is likewise known that nitrogen dioxide $NO_2$ absorbs up to 650 nm, and thus in the entire range between 200 nm and 400 nm. The first and second optoelectronic sensors 2, 4 have sensitivity bands that are thus a function of the spectra of absorption of nitrogen monoxide NO and nitrogen dioxide $NO_2$. Further, the first and second optoelectronic sensors 2, 4 are substantially insensitive to radiation having a wavelength, respectively, falling outside the first and second ranges.

For practical purposes, the intensity of the radiation that impinges upon the first and second optoelectronic sensors 2, 4, after having traversed the fluid F, may be determined on the basis of the so-called Lambert-Beer law. In particular, on the hypothesis of having a monochromatic radiation and an fluidic absorber formed by just one type of chemical species and with a concentration equal to C, the Lambert-Beer law envisages that $$I(\lambda,x)=I_0(\lambda)\cdot e^{-x\cdot\sigma(\lambda)C}$$

where $I_0(\lambda)$ is the intensity of the monochromatic radiation that impinges upon the absorber, and $\sigma(\lambda)$ is the absorption cross-section for the chemical species at the wavelength of the monochromatic radiation; further, $I(\lambda, x)$ is the intensity of the radiation after it has covered an optical path of length x within the absorber. Consequently, knowledge of the intensities $I_0(\lambda)$ and $I(\lambda, x)$, of the distance x, and of the absorption cross-section $\sigma(\lambda)$ enables determination of the concentration C, which is assumed as being constant for the distance x.

In greater detail, in what follows it is assumed that the optical source 20 is at a distance x both from the first optoelectronic sensor 2 and from the second optoelectronic sensor 4. More in particular, it is assumed that the first and second optical paths that connect the optical source 20 to the first and second optoelectronic sensors 2, 4 respectively, both have a length x and extend, in use, entirely through the fluid F. Furthermore, it is assumed that the absorption of radiation generated by the optical source 20 in the range 200-400 nm by chemical species different from nitrogen monoxide NO and nitrogen dioxide $NO_2$ (for example, sulphur dioxide $SO_2$) is negligible. In addition, in what follows the portion of the radiation generated by the optical source 20 in the range 200-230 nm and incident, in the absence of the fluid F, upon the first optoelectronic sensor 2 will be referred to as "first detection beam". Instead, the portion of the radiation generated by the optical source 20 in the range 230-400 nm and incident, in the absence of the fluid F, upon the second optoelectronic sensor 4 will be referred to as "second detection beam".

This being said, the first optoelectronic sensor 2 detects the portion of the first detection beam not absorbed either by nitrogen monoxide NO or by nitrogen dioxide $NO_2$, which depends upon the concentrations and upon the absorption cross-sections of these two chemical species. In addition, the second optoelectronic sensor 4 detects the portion of the second detection beam not absorbed by nitrogen dioxide $NO_2$, which depends upon the concentration and upon the absorption cross-section for nitrogen dioxide $NO_2$. The first and second detection signals, which are formed by photocurrents, thus indicate, respectively, i) the combination of the concentrations of nitrogen monoxide NO and nitrogen dioxide $NO_2$, and ii) the concentration of nitrogen dioxide $NO_2$.

In greater detail, with reference to the intensity of the radiation that impinges upon the first optoelectronic sensor 2, this is equal to $$I_1 = I_{10} \int e^{-x \cdot [\sigma 1(\lambda) \cdot C1 + \sigma 2(\lambda) \cdot C2]} d\lambda$$

where $I_{10}$ is the (known) intensity of the aforementioned first detection beam, $\sigma 1(\lambda)$ is the absorption cross-section for nitrogen monoxide NO, $\sigma 2(\lambda)$ is the absorption cross-section for nitrogen dioxide $NO_2$, and C1 and C2 are, respectively, the concentrations of nitrogen monoxide NO and nitrogen dioxide $NO_2$ in the fluid F. Consequently, the first detection signal and the first processable signal, which are proportional to the intensity $I_1$, are a function of the concentrations of nitrogen monoxide NO and nitrogen dioxide $NO_2$.

With reference to the intensity of the radiation that impinges upon the second optoelectronic sensor 4, this is equal to $$I_2 = I_{20} \int e^{-x \cdot [\sigma 3(\lambda) \cdot C2]} d\lambda$$

where $I_{20}$ is the (known) intensity of the aforementioned second detection beam, and $\sigma 3(\lambda)$ is the absorption cross-section for nitrogen dioxide $NO_2$. Consequently, the second detection signal and the second processable signal, which are proportional to the intensity $I_2$, are a function of the concentration of nitrogen dioxide $NO_2$.

On the basis of the first and of the second processable signal, the processing unit 12 is thus able to determine each one between the concentration of nitrogen monoxide NO and the concentration of nitrogen dioxide $NO_2$. Without this implying any loss of generality, it is assumed that the above two concentrations are constant along the optical paths covered by the first and second detection beams.

In greater detail, in a per se known manner, the processing unit 12 numerically determines the concentration C2 of nitrogen dioxide $NO_2$, on the basis of a measurement of the intensity $I_2$, as determined by the processing unit 12 itself on the basis of the second processable signal. Next, the processing unit 12 numerically determines the concentration C1 of nitrogen monoxide NO, on the basis of the concentration C2 of nitrogen dioxide $NO_2$ and of a measurement of the intensity $I_1$, as determined by the processing unit 12 itself on the basis of the first processable signal. More precisely, the processing unit 12 determines estimates of the aforementioned concentrations C1 and C2.

Purely by way of example, in the numerical processing, the processing unit 12 may be based upon the use of the following approximate relations:

$$I_1 = I_{10} \cdot e^{-x \cdot [\sigma 1 m \cdot C1 + \sigma 2 m \cdot C2]}$$

$$I_2 = I_{20} \cdot e^{-x \cdot \sigma 3 m \cdot C2}$$

where $\sigma 1m$ is the integral of the absorption cross-section for nitrogen monoxide NO in the range 200-230 nm, $\sigma 2m$ is the integral of the absorption cross-section for nitrogen dioxide $NO_2$ in the range 200-230 nm, and $\alpha 3m$ is the integral of the absorption cross-section for nitrogen dioxide $NO_2$ in the range 230-400 nm.

Figure 5:
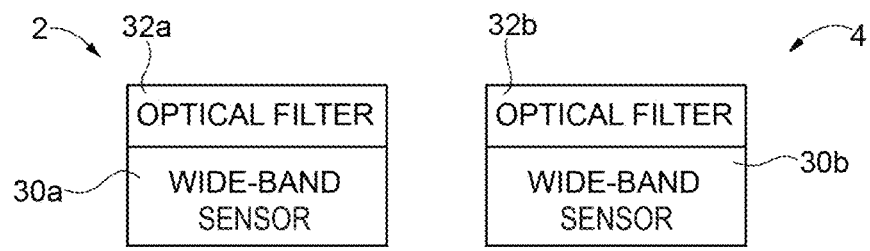
FIG. 5 shows a block diagram of an embodiment of a first optoelectronic sensor and a second optoelectronic sensor that form the present detection device.

As illustrated qualitatively in FIG. 5, the first optoelectronic sensor 2 may be formed by a first wide-band sensor 30a, having a band at least equal to 200-400 nm, and by a first optical filter 32a, having a passband of 200-230 nm and arranged over the first wide-band sensor 30a. The first optical filter 32a may be formed in a per se known manner by a plurality of dielectric layers; further, the first optical filter 32a may be integrated with the first wide-band sensor 30a, or else may be physically separate from the latter. Likewise, the second optoelectronic sensor 4 may be formed by a second wide-band sensor 30b, having a band at least equal to 200-400 nm, and by a second optical filter 32a, having a passband of 230-400 nm and arranged over the second wide-band sensor 30b. The second optical filter 32b may be formed in a per se known manner by a plurality of dielectric layers; further, the second optical filter 32b may be integrated with the second wide-band sensor 30b, or else may be physically separate from the latter.

According to the embodiment illustrated in FIGS. 6 and 7, the first and second optoelectronic sensors 2, 4 are integrated with one another and form a semiconductor device of a monolithic type.

In detail, the detection device 1 comprises a semiconductor body 40 of silicon carbide SiC of the 4H type, which in turn comprises a substrate 42 and an epitaxial layer 44, formed on the substrate 42.

In greater detail, the substrate 42 is of an N type (for example, doped with nitrogen), has a thickness of, for example, 350 μm and has a doping level of, for example, $10^{19}$ $cm^{-3}$. The epitaxial layer 44 is of N-type (for example, doped with nitrogen) and has a doping level of, for example, $10^{14}$ $cm^{-3}$. Further, the epitaxial layer 44 includes a first epitaxial region 45 and a second epitaxial region 46, arranged alongside one another, the first epitaxial region 45 having a thickness comprised, for example, in the range 0.3-0.5 μm, and the second epitaxial region 46 having a thickness comprised, for example, in the range 4-6 μm. The first and second epitaxial regions 45, 46 are delimited at the top by a first top surface $S_{a1}$ and a second top surface $S_{a2}$, respectively, whereas the substrate 42 is delimited at the bottom by a bottom surface $S_b$.

The semiconductor body 40 further comprises a first anode region 48 and a second anode region 50, of a P+ type (for example, doped with aluminium) and with peak doping level of approximately $10^{18}$ $cm^{-3}$. More in particular, the first anode region 48 extends within the first epitaxial region 45, starting from the first top surface $S_{a1}$ and with a thickness comprised, for example, in the range 0.1-0.2 μm. Furthermore, the second anode region 50 extends within the second epitaxial region 46, starting from the second top surface $S_{a2}$ and with a thickness comprised, for example, in the range 0.1-0.2 μm. Consequently, the first and second anode regions 48, 50 overlie, respectively, a portion of the first epitaxial region 45 and a portion of the second epitaxial region 46, which have thicknesses, respectively, comprised, for example, in the ranges 0.1-0.4 µm and 3.8-5.9 µm.

Figure 8:
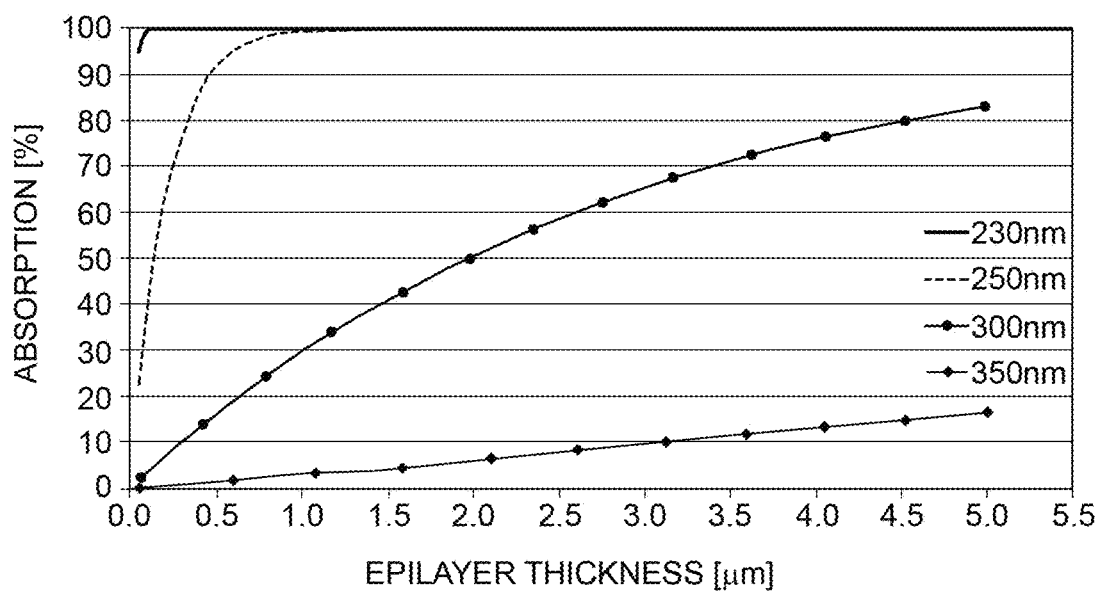
FIG. 8 shows the plot of the absorption of radiation having a wavelength alternatively equal to 230 nm, 250 nm, 300 nm, and 350 nm within a silicon-carbide junction of the 4H type, as a function of the thickness of the epilayer (on the hypothesis of fully depleted epilayer)

The first anode region 48 and the first epitaxial region 45 form the first optoelectronic sensor 2, and in particular form a first PN junction, where the so-called "epilayer", formed by the portion of the first epitaxial region 45 underlying the first anode region 48, has a thickness comprised in the range 0.1-0.4 µm. This first PN junction is thus rather shallow and is arranged in the proximity of the first top surface $S_{a1}$. This implies, as illustrated in FIG. 8, that substantially all the radiation that traverses the first PN junction and has a wavelength shorter than 230 nm is absorbed by the junction itself.

The second anode region 50 and the second epitaxial region 46 form the second optoelectronic sensor 4, and in particular form a second PN junction, where the so-called "epilayer" has a large thickness. Furthermore, present on a first portion of the second anode region 50 is an absorption layer 59, for example, of polysilicon and having the function of absorbing radiation having a wavelength shorter than 230 nm, before it impinges upon the second PN junction. For instance, the absorption layer 59 may have a thickness comprised in the range 10-50 nm.

The detection device 1 likewise comprises a first anode metallization 60 and a second anode metallization 62, which are, for example, of titanium and an AlSiCu alloy (for simplicity of exposition, the distinction between titanium and AlSiCu alloy is not illustrated in FIG. 7). Furthermore, the first and second anode metallizations 60, 62 are arranged, respectively, on the first and second anode regions 48, 50, with which they are, respectively, in direct contact. In particular, without this implying any loss of generality, the second anode metallization 62 extends over a second portion of the second anode region 50 so as to be laterally staggered with respect to the absorption layer 59. Further, the first anode metallization 60 extends over a side portion of the first anode region 48.

The detection device 1 further comprises a layer 66, which will be referred to hereinafter as "contact layer 66". The contact layer 66 is arranged underneath the bottom surface $S_b$ and is, for example, of nickel silicide $Ni_2Si$; purely by way of example, the contact layer 66 may have a thickness of, for example, 40 nm. Furthermore, the detection device 1 comprises a cathode metallization 68, arranged underneath the contact layer 66 and formed for example by a multilayer structure including layers (not illustrated individually) formed by titanium, nickel, and gold.

In practice, the first and second epitaxial regions 45, 46 form corresponding cathode regions. Furthermore, the low doping level of the epitaxial layer 44 causes, even in the absence of biasing, complete depletion both of the portion of the first epitaxial region 45 overlaid by the first anode region 48 and of the portion of the second epitaxial region 46 overlaid by the second anode region 50. Furthermore, both the first and the second optoelectronic sensors 2, 4 can be biased simultaneously through the cathode metallization 68, while the first and second detection signals generated by them can be acquired, respectively, at the first and second anode metallizations 60, 62.

According to a different embodiment (illustrated in FIG. 9), each one of the first and second optoelectronic sensors 2, 4 includes a Schottky junction, as well as a PN junction.

In detail, the detection device 1 comprises, instead of the first and second anode regions 48, 50, a first metal region 70 and a second metal region 72, which extend, respectively, on the first and second top surfaces $S_{a1}$, $S_{a2}$ so as to contact directly the first and second epitaxial regions 45, 46, respectively. In this case, the first and second epitaxial regions 45, 46 have thicknesses, respectively, comprised, for example, in the ranges 0.1-0.4 µm and 3.8-5.9 µm. The first and second anode metallizations 60, 62 contact, respectively, the first and second metal regions 70, 72. Further, the second metal region 72 is overlaid by the absorption layer 59.

Without this implying any loss of generality, in what follows a method is described for manufacturing the embodiment illustrated in FIG. 7.

Figure 9:
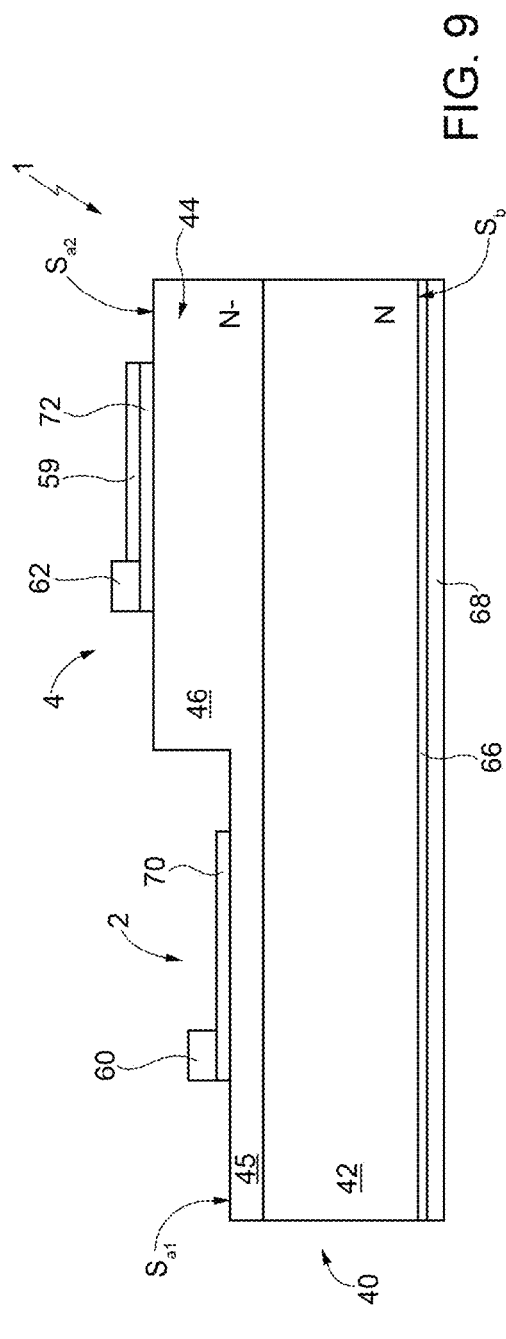
FIG. 9 is a schematic cross-sectional view of a further embodiment of the present detection device.
Figure 10:
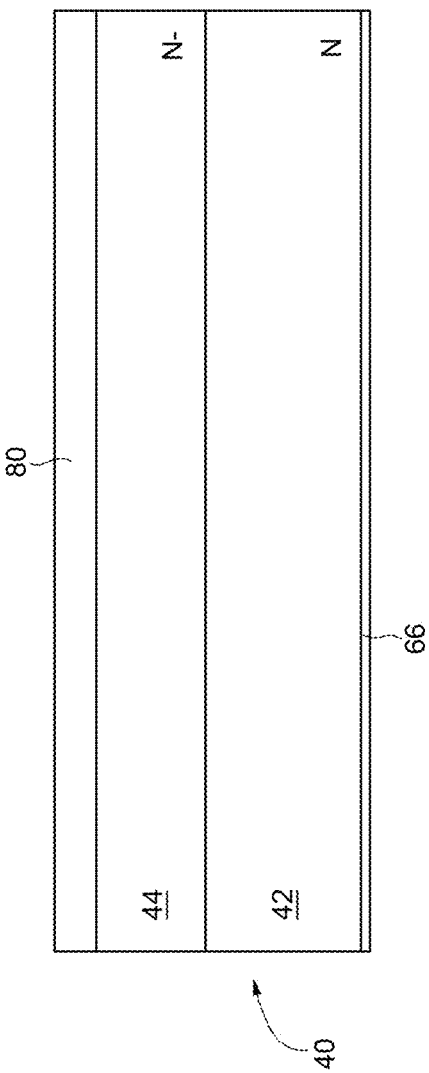

Initially, as illustrated in FIG. 10, the semiconductor body 40 made up of the substrate 42 and the epitaxial layer 44 is formed. Furthermore, formed on the epitaxial layer 44 is a first layer of TEOS oxide 80 having a thickness of, for example, 20 µm (FIG. 10, as on the other hand also the subsequent figures, as well as FIGS. 6, 7 and 9 are not in scale). Then, formed underneath the substrate 42 is the contact layer 66, for example by sputtering and subsequent annealing, the latter being carried out, for example, at 1000° C., in the presence of nitrogen $N_2$, and having a duration of one minute.

Figure 11:
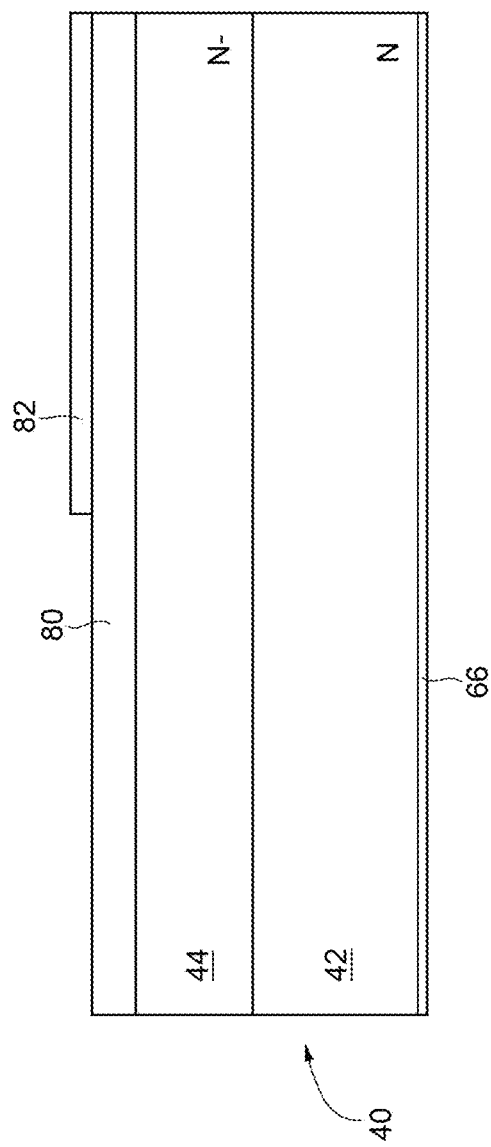

Next, as illustrated in FIG. 11, provided on the first layer of TEOS oxide is a first mask 82, for example a resist mask.

Figure 12:
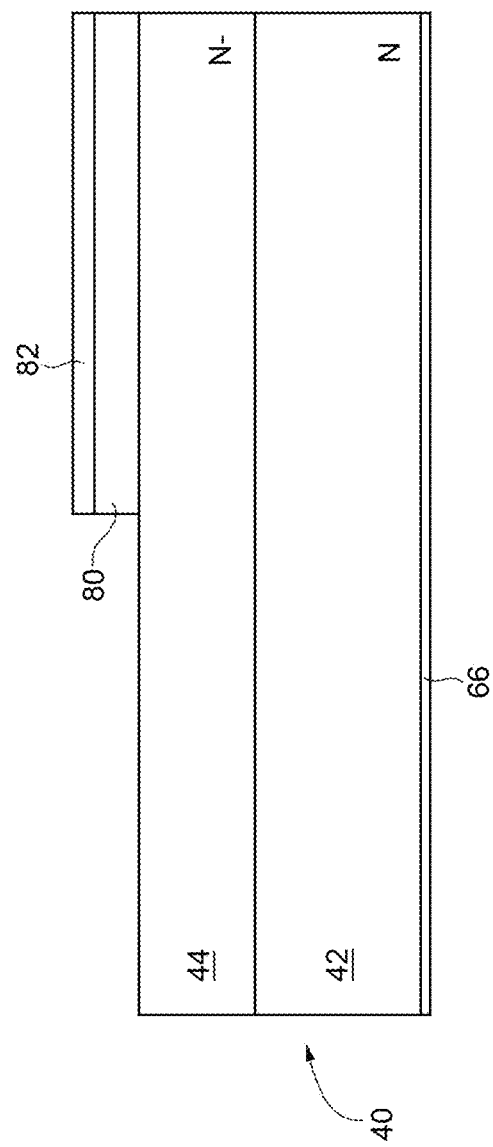

Then, as illustrated in FIG. 12, a process of photolithography is carried out in order to remove a portion of the first layer of TEOS oxide 80 so as to expose a part of the epitaxial layer 44. Then, the first mask 82 is removed.

Next, as illustrated in FIG. 13, a process of reactive ion etching (RIE) is carried out so as to form the first and second epitaxial regions 45, 46, as well as the first and second top surfaces $S_{a1}$, $S_{a2}$. In particular, a top portion of the exposed part of the epitaxial layer 44 is selectively removed in order to form the first epitaxial region 45. Then, the residual portion of the first layer of TEOS oxide 80 is removed.

Next, as illustrated in FIG. 14, formed on the first and second top surfaces $S_{a1}$, $S_{a2}$ is a second layer of TEOS oxide 84, which has a thickness comprised, for example, between 50 nm and 100 nm.

Figure 15:
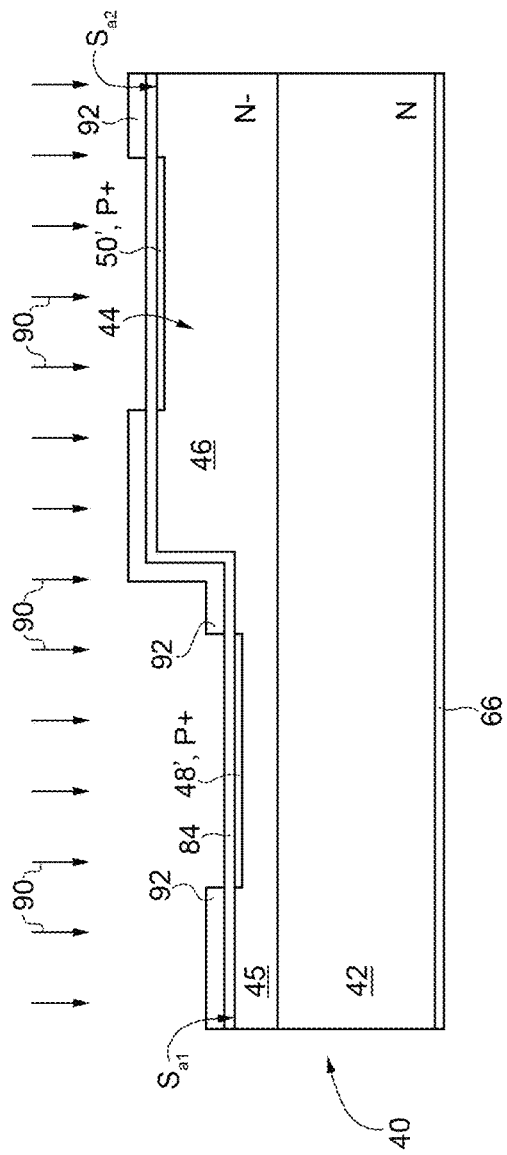

Then, as illustrated in FIG. 15, by a process of photolithography and a subsequent ion-implantation of dopant species of a P type, a first thin layer 48' and a second thin layer 50' are formed, which extend, respectively, in the first and second epitaxial regions 45, 46, starting from the first top surface $S_{a1}$ and the second top surface $S_{a2}$, respectively. In addition, the first and second thin layers 48', 50' are to form, respectively, the first and second anode regions 48, 50, once the appropriate thermal treatments are terminated, as explained hereinafter.

In greater detail, the aforementioned step of ion implantation, indicated by the arrows 90, may comprise a plurality of high-dosage implants ($5 \cdot 10^{14} - 3 \cdot 10^{15}$ cm$^{-2}$) and increasing energy (for example, in the range 50-200 keV), at a temperature of 400° C., and envisages the use of a second resist mask 92 for reducing the contamination of sites external to the regions in which the implantation itself is to be carried out.

Figure 16:
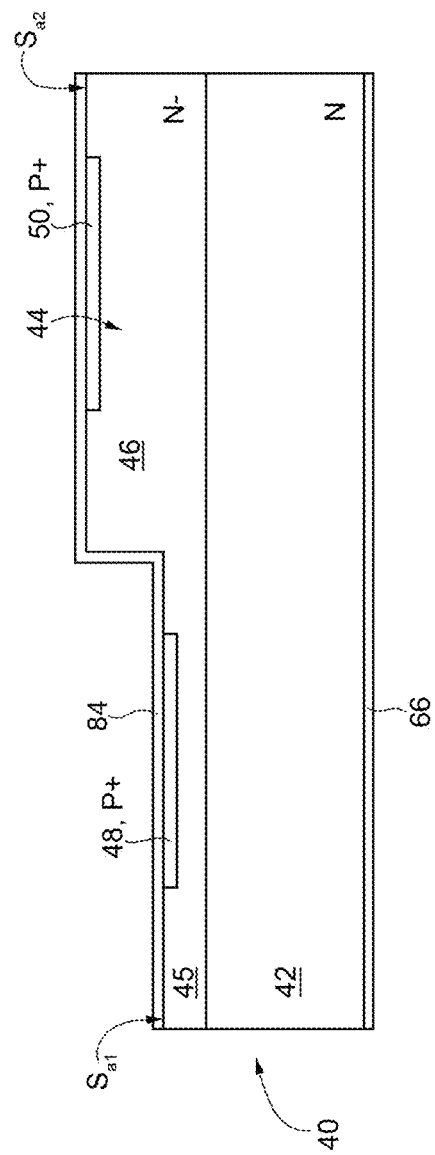

Next, as illustrated in FIG. 16, the second mask 92 is removed, for example by a further wet etch, and annealing is carried out, which enables formation of the first and second anode regions 48, 50, respectively, starting from the first and second thin layers 48', 50'.

Next, as illustrated in FIG. 17, the second layer of TEOS oxide 84 is removed. Furthermore, deposited on the first and second top surfaces $S_{a1}$, $S_{a2}$ is a polysilicon layer 100 having, for example, a thickness comprised in the range 10-50 nm. Provided on the polysilicon layer 100 is a third mask 102.

Next, as illustrated in FIG. 18, a further process of photolithography is carried out in order to remove selectively portions of the polysilicon layer 100, for example by a wet etch so as to form the absorption layer 59. Then, the third mask 102 is removed.

Next, as illustrated in FIG. 18, formed on the first and second top surfaces $S_{a1}$, $S_{a2}$, as well as on the absorption layer 59, is a barrier layer 110, for instance, of titanium and having a thickness of, for example, 100 nm. In addition, formed on the barrier layer 110 is a functional layer 112 of a metal type, for example, of the AlSiCu alloy. Both the barrier layer 110 and the functional layer 112 may be obtained by sputtering.

Next, as illustrated in FIG. 19, portions of the barrier layer 110 and of the functional layer 112 are selectively removed, for example by a wet etch, so as to form the first and second anode metallizations 60, 62.

Finally, in a way not illustrated, the cathode metallization 68 is formed, for example by sputtering, underneath the contact layer 66.

In the case where, instead, an embodiment is adopted in which the first and second optoelectronic sensors form respective Schottky junctions, this may be obtained by carrying out the operations illustrated in FIGS. 10-13. Next, as illustrated in FIG. 20, a metal layer 130 is formed on the first and second epitaxial regions 45, 46, which is then patterned, by selective removal of portions, so as to form the first and second metal regions 70, 72. The absorption layer 59 and the first and second anode metallizations 60, 62 are then formed as described previously, but on the first and second metal regions 70, 72.

From what has been described and illustrated previously, the advantages that the present solution affords emerge clearly.

In particular, the present detection device enables simultaneous detection of the concentrations of two different chemical species, with a high sensitivity.

For this purpose, the first and second optoelectronic sensors are illuminated simultaneously by the optical source.

Furthermore, in the case where the first and second optoelectronic sensors are of silicon carbide, the sensitivity is kept high also at high temperature, thanks to the low leakage currents in the silicon carbide. Further, both the first optoelectronic sensor and the second optoelectronic sensor may be reverse biased with very low voltages (in modulus), possibly even in the photovoltaic regime. In addition, the first and second optoelectronic sensors can operate also in the presence of chemical agents and have characteristics that remain very stable over time.

Furthermore, in the case where the first and second optoelectronic sensors are integrated with one another, the detection device has very small overall dimensions. Again, the detection device may readily be adapted to different pairs of chemical species by varying the thickness and the material of the epitaxial layer accordingly. In addition, the detection device may be used not only in the presence of a flow of fluid, but also in the presence of a fluid substantially at rest, or even in the presence of a solid containing the chemical species to be detected.

In conclusion, it is clear that modifications and variations may be made to what has been described and illustrated herein, without thereby departing from the scope of the present disclosure.

As mentioned previously, the first and second optoelectronic sensors may be sensors of a different type, such as for example vacuum photomultiplier tubes (PMTs). Furthermore, in the case where the first and second sensors are again semiconductor sensors integrated together, the semiconductor body may be formed by a semiconductor material different from silicon carbide, such as for example silicon, or else gallium nitride GaN or aluminium gallium nitride AlGaN.

In addition, the first and the second sensitivity bands, which correspond, respectively, to the first and second optoelectronic sensors, may be separate from one another. It is likewise possible for the first and second sensitivity bands to be instead partially overlapping in an intersection range. In this case, it is possible, but not necessary, for the absorption cross-section for at least one of the first and second chemical species to be zero within the intersection range. In general, even though the fact that the absorption cross-section for a chemical species is zero in the second absorption band simplifies the operations performed by the processing unit 12, it is in any case possible that in each one of the first and second sensitivity bands the absorption cross-sections for both of the chemical species to be detected are at least locally (i.e., in a portion of the sensitivity range) nonzero. In this case, with reference, for example, once again to nitrogen monoxide NO and nitrogen dioxide $NO_2$, the intensity of the radiation that impinges upon the second optoelectronic sensor is equal to $$I_2 = I_{20} \int e^{-x \cdot [\sigma 4(\lambda) \cdot C1 + \sigma 3(\lambda) \cdot C2]} d\lambda$$

where $\sigma 4(\lambda)$ is the absorption cross-section for nitrogen oxide NO. The latter relation may be approximated as:

$$I_2 = I_{20} \cdot e^{-x \cdot [\sigma 4m \cdot C1 + \sigma 3m \cdot C2]}$$

where $\sigma 4m$ is the integral of the absorption cross-section for nitrogen oxide NO in the second sensitivity band. The processing unit 12 can thus determine the concentrations C1 and C2 by solving a system of two equations with two unknowns, on the basis of the intensities $I_1$ and $I_2$.

In general, it is further possible for the optical source to have a non-constant spectrum, in which case the numeric processing operation executed by the processing unit 12 is modified in a per se known manner.

As regards the processing unit 12, this may be integrated in the semiconductor body 40, and thus may be integrated with the first and second optoelectronic sensors 2, 4, or else may be external to the latter.

As regards the first and second anode regions, when these are arranged on the first and second top surfaces $S_{a1}$, $S_{a2}$, they may be formed by a non-metal conductive material, such as for example polysilicon. Consequently, the first and second metal regions 70, 72 may be replaced by corresponding non-metal conductive regions, for instance of polysilicon. In this case, during manufacture, a corresponding conductive layer is formed, instead of the metal layer 130.

As regards the absorption layer 59, this may be of a material different from polysilicon, such as silicone, or else an optically absorbent metal material, such as titanium nitride TiN.

Finally, all the types of doping may be reversed with respect to what has been described.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An optical device, comprising:
   an optical source;
   a first optical sensor configured to be optically coupled to the optical source through a specimen, the specimen having a first chemical species and a second chemical species, the first optical sensor being sensitive to radiation having a wavelength in a first range of wavelengths; and
   a second optical sensor configured to be optically coupled to the optical source through the specimen, the second optical sensor being sensitive to radiation having a wavelength in a second range of wavelengths, different from the first range of wavelengths.

2. The device of claim 1 wherein the first and second chemical species have, respectively, a first absorption cross-section and a second absorption cross-section; and in the first range of wavelengths, both the first and the second absorption cross-sections are at least locally nonzero; and in the second range of wavelengths, the first absorption cross-section is substantially zero and the second absorption cross-section is at least locally nonzero.

3. The device of claim 2 wherein the first and second optical sensors are configured to generate, respectively, a first electrical signal and a second electrical signal, said device further comprising a processing stage configured to determine an estimate of concentrations of the first and second chemical species as a function of the first and second electrical signals.

4. The device of claim 3 wherein the processing stage is configured to determine:
   the estimate of the concentration of the second chemical species on the basis of the second electrical signal;
   the estimate of the concentration of the first chemical species on the basis of the estimate of the concentration of the second chemical species and of the first electrical signal.

5. The device of claim 1 wherein the first and second optical sensors are semiconductor sensors.

6. The device of claim 5, further comprising a semiconductor body, the first and second optical sensors formed at least in part by the semiconductor body.

7. The device of claim 6 wherein the semiconductor body includes a substrate, a cathode region, a first epitaxial region, and a second epitaxial region, all arranged on the substrate, the first and second epitaxial regions having different thicknesses; said device further including a first anode region and a second anode region, arranged, respectively, in contact with the first and second epitaxial regions to form, respectively, a first junction and a second junction.

8. The device of claim 7 wherein the first and second epitaxial regions are of a first type of conductivity and are delimited, respectively, by a first front surface and a second front surface; and the first and second anode regions are formed by semiconductor material of a second type of conductivity, the first anode region extending within the first epitaxial region, starting from the first front surface, the second anode region extending within the second epitaxial region, starting from the second front surface.

9. The device of claim 7 wherein the first and second epitaxial regions are delimited, respectively, by a first front surface and a second front surface; and the first and second anode regions are formed by conductive material and extend, respectively, over the first and second front surfaces.

10. The device of claim 8, further comprising an optically absorbent region that is optically absorbent in the first range of wavelengths and is on top of the second anode region.

11. The device of claim 7 wherein the semiconductor body is of silicon carbide.

12. The device of claim 11 wherein the first epitaxial region includes a respective portion which extends underneath the first anode region and has a thickness comprised in the range 0.1-0.4 µm; and the second epitaxial region includes a respective portion which extends underneath the second anode region and has a thickness comprised in the range 3.8-5.9 µm.

13. The device of claim 1 wherein the first chemical species includes nitrogen monoxide and the second chemical species comprises nitrogen dioxide; and the second range of wavelengths does not extend below 230 nm.

14. A method, comprising:
   manufacturing an optical device for detecting a first chemical species and a second chemical species in a specimen, the method including:
   forming a first optical sensor configured to be optically coupled to an optical source through the specimen, is the first optical sensor being sensitive to radiation having a wavelength in a first range of wavelengths; and
   forming a second optical sensor configured to be optically coupled to the optical source through the specimen, the second optical sensor being sensitive to radiation having a wavelength comprised in a second range of wavelengths, different from the first range of wavelengths.

15. The method of claim 14, comprising forming a cathode region, the forming of the cathode region including:
   providing a semiconductor body having a substrate and an epitaxial layer;
   forming a first epitaxial region and a second epitaxial region having different thicknesses by selectively removing a portion of the epitaxial layer, the first and second epitaxial regions being laterally staggered and delimited, respectively, by a first front surface and a second front surface; and
   forming a first anode region and a second anode region in contact with the first and second epitaxial regions, respectively.

16. The method according to claim 15 wherein the forming of the first anode region and the second anode region includes selectively implanting ions in a portion of the first epitaxial region and in a portion of the second epitaxial region.

17. The method of claim 15 wherein the forming of the first anode region and the second anode region includes forming a layer of conductive material on the first and second epitaxial regions, and then selectively removing portions of the layer of conductive material.

18. The method of claim 16, further comprising forming an optically absorbent region that is optically absorbent in the first range of wavelengths, on the second anode region.

19. A device, comprising:
   a substrate;
   a first optical sensor formed in the substrate, the first optical sensor being sensitive to radiation having a wavelength in a first range of wavelengths, the first optical sensor being configured to detect a first chemical species in a specimen; and
   a second optical sensor formed in the substrate adjacent to the first optical sensor, the second optical sensor being sensitive to radiation having a wavelength in a second range of wavelengths, different from the first range of wavelengths, the second optical sensor being configured to detect a second chemical species in the specimen.

20. The device of claim 19, further comprising an optical source that is separated from the first and second optical sensors by the specimen.

21. The device of claim 20, further comprising a specimen inlet positioned adjacent to the optical source and a specimen outlet positioned adjacent to the first and second optical sensors.

22. The device of claim 19, further comprising a first epitaxial region and a second epitaxial region on the substrate, the first optical sensor being formed on the first epitaxial region and the second optical sensor being formed on the second epitaxial region.

* * * * *